United States Patent
Berger et al.

(10) Patent No.: US 8,323,680 B1
(45) Date of Patent: Dec. 4, 2012

(54) NUTRITIONAL COMPOSITION

(75) Inventors: Alvin Berger, Lausanne (CH); Gayle Crozier, Lausanne (CH)

(73) Assignee: Nestec S.A., Vevey (CH)

( * ) Notice: Subject to any disclaimer, the term of this patent is extended or adjusted under 35 U.S.C. 154(b) by 954 days.

(21) Appl. No.: 10/089,658

(22) PCT Filed: Sep. 14, 2000

(86) PCT No.: PCT/EP00/08995
§ 371 (c)(1),
(2), (4) Date: Jul. 22, 2002

(87) PCT Pub. No.: WO01/24645
PCT Pub. Date: Apr. 12, 2001

(30) Foreign Application Priority Data

Oct. 7, 1999 (GB) .................................. 9923738.0

(51) Int. Cl.
*A61K 47/00* (2006.01)
(52) U.S. Cl. .................... 424/439; 514/959; 514/960
(58) Field of Classification Search .................... 424/439
See application file for complete search history.

(56) References Cited

U.S. PATENT DOCUMENTS

| | | | | |
|---|---|---|---|---|
| 5,411,751 | A * | 5/1995 | Crissinger et al. | 426/2 |
| 5,618,955 | A * | 4/1997 | Mechoulam et al. | 554/66 |
| 5,874,459 | A * | 2/1999 | Makriyannis et al. | 514/425 |
| 6,552,031 | B1 * | 4/2003 | Burch et al. | 514/282 |
| 2004/0127518 | A1 * | 7/2004 | Piomelli et al. | 514/332 |

FOREIGN PATENT DOCUMENTS

| | | |
|---|---|---|
| EP | 0 409 559 A2 | 1/1991 |
| EP | 0 490 561 A2 | 6/1992 |
| EP | 0 733 360 A2 | 9/1996 |
| WO | WO 94/12466 | 6/1994 |
| WO | WO 94/28913 | 12/1994 |
| WO | WO 9428913 A1 * | 12/1994 |
| WO | WO 96/37200 | 11/1996 |
| WO | WO 9637200 A1 * | 11/1996 |
| WO | WO 96/40106 | 12/1996 |

OTHER PUBLICATIONS

Di Marzo V. 2-Arachidonoyl-glycerol as an "endocannabinoid": limelight for a formerly neglected metabolite, Biochemistry (Mosc). Jan. 1998;63(1):13-21.*
Eric Murillo-Rodriguez et al. Anandamide modulates sleep and memory in rats, Brain Research, vol. 812, Issues 1-2, Nov. 23, 1998, pp. 270-274.*
Bennett et al. "Suppression of Renal Inflammation With Vitamins A and E in Ascending Pyelonephritis in Rat", The Journal of Urology, vol. 161, Issue 5, May 1999, pp. 1681-1684.*
Kajiwara article entitled: "An Antiulcerative Action of Active Metabolite of Gefarnate, Farnesylacetic Acid" *J. Med. Soc. Toho, Japan*, (1985) 32(1): 108-119.
Toft et al. article entitled: "Effects of n-3 Polyunsaturated Fatty Acids on Glucose Homeostatis and Blood Pressure in Essential Hypertension" *Annals of Internal Medicine*, vol. 123, No. 12, Dec. 15, 1995.
Rossetti et al. article entitled: "Oral Administration of Unsaturated Fatty Acids: Effects on Human Peripheral Blood T Lymphocyte Proliferation" *Journal of Leukocyte Biology*, vol. 62, Oct. 1997.
Focant et al. article entitled: "The Effect of Vitamin E Supplementation of Cow Diets Containing Rapeseed and Linseed on the Prevention of Milk Fat Oxidation" *J. Dairy Sci.*, 81:1095-1101, 1998.

* cited by examiner

*Primary Examiner* — James Rogers
(74) *Attorney, Agent, or Firm* — K&L Gates LLP

(57) ABSTRACT

A nutritional or therapeutic composition for oral administration which comprises a naturally occurring precursor that is metabolised to a compound having anandamide activity for use as a medicament or nutritive product. In addition the invention includes a method of production of the composition, use of the composition in the manufacture of a nutritional composition for the treatment or prevention of a behavioral disorder; and a method of treatment or prevention of a behavioral disorder which comprises administering an effective amount of the composition. In a preferred embodiment the composition comprises a triacylglycerol having palmitate and arachidonate attached to its backbone wherein arachidonate is at the sn-1 and sn-2 positions.

11 Claims, 7 Drawing Sheets

NUTRITIONAL COMPOSITION

The present invention relates to a nutritional or therapeutic composition for oral administration which comprises a naturally occurring precursor that is metabolised to a compound having anandamide activity for use as a medicament or nutritional product, a method of production of the composition, use of the composition in the manufacture of a nutritional or therapeutic composition for the treatment or prevention of a behavioural disorder; and a method of treatment or prevention of a behavioural disorder which comprises administering an effective amount of the composition.

Within the context of this specification the word "comprises" is taken to mean "includes, among other things". It is not intended to be construed as "consists of only".

Standard nomenclature for fatty acid compounds is used. For example, the number of carbon atoms and number and position of double bonds is typified by "20:4(5,8,11,14)" for arachidonic acid: the number preceding the colon is the total number of carbon atoms, the number immediately following the colon is the number of double bonds, and the numbers in parentheses are the position of the double bonds, starting from the end of the chain bearing the carboxylic acid group. In all compounds referred to in this manner, except where otherwise indicated, all double bonds are cis.

Standard nomenclature for classes of fatty acid compounds is used indicating the location of the double bond closest to the methyl end group, typified by "n-3" or "n-6": the number following the dash denotes the position of the double bond closest to the methyl end of the molecule, counting from the methyl end. Thus, arachidonic acid is in the n-6 class, as is linoleic acid (18:2(9,12)), whereas eicosapentaenoic acid (20:5(5,8,11,14,17)) is in the n-3 class. This nomenclature is equivalent to "omega or ω" nomenclature in the literature, "ω" and "n" being interchangeable.

Anandamide (also referred to as N-arachidonylethanolamine) is an example of an N-acyl ethanolamine (hereinafter referred to as NAE). Both NAEs and N-acyl amines (hereinafter referred to as NAAs), an example of the latter of which is oleamide, are naturally occurring in the human body. They have been found in the hippocampus, striatum, cerebellum, spleen, heart, plasma and cerebral spinal fluid as well as in human milk.

The term "anandamide activity" is used within the context of this specification to mean an activity selected from the group which comprises an activity attributed to the drug 9-tetrahydrocannabinol (THC), as well as affects specific to anandamide and 1- and 2-monoarachidonylglycerol isomers (hereafter denoted AG), and unique from THC. It has been suggested that anandamide and AG activities are typically, but not necessarily, mediated by binding to the receptor class, known as CB1 and CB2 receptors. These anandamide activities include, but are not limited to: antinociception, catalepsy and inhibition of locomotor activity in vivo and displacement of 9-tetrahydrocannabinol (THC), inhibition of adenylate cyclase, inhibition of calcium channels, activation of phospholipase $A_2$, release of intracellular calcium in vitro and inhibition of twitch response ex vivo.

The term anandamide, as used within the context of this specification, refers to an NAE, NAA or MAG having anandamide activity (as defined above). Accepted scientific nomenclature will be used in this specification when reference is made to specific acyl moieties of an NAE, NAA or MAG.

It is well known that pharmaceutical compounds have wide application for their calming effects and they may be used in the treatment of patients suffering from conditions such as hypertension, glaucoma, insomnia, pain, inflammation, migraine headaches, convulsions, loss of appetite, nausea, cramps, diarrhea, asthma, nervousness, aggressive behaviour, excessive timidity, inability to sleep, catalepsy, low mood, depression, gut upsets, or spasms, poor motor control, tics, excessive stress, spasticity or multiple sclerosis. However, a number of these compounds are not naturally occurring in nature and in view of this, patients may be reluctant to be administered them. In the light of this there is a need for the provision of new products which include naturally occurring precursors of compounds that have a nutritive or therapeutic effect, when metabolised endogenously to active compounds with anandamide activity.

Furthermore, a problem with most commercially available drugs is that they give rise to side affects such as nausea, bloating, cramping, etc. Clearly there is a need for a composition which does not give rise to these side effects.

The method of administration of a nutritive or therapeutic compound is an important consideration. Intravenous or subcutaneous administration of drugs requires expertise, and compared to oral administration it is not as safe, convenient or acceptable to the patient. In the light of these concerns it is clear that there is a need for new nutritive or therapeutic products which may be administered orally.

In addition to the problems set out above, infant formulae are generally constructed so that they resemble human milk as closely as possible, however a plurality of components in human milk are bioactive and, because of synergies among the components, the inclusion of only one or a few of them may not reproduce the bioactivity of human milk. In view of this, a problem which presently faces researchers lies in the formulation of infant formulae or weaning foods which have components that are present in human milk and which have an equivalent activity to human milk. The problem is compounded in view of the fact that not all of the components in human milk have been identified and there are variations in the concentration of components which are present, possibly due to variations of mother's diets.

A further problem which faces nutritionists lies in the field of pet nutrition. Whereas some pets are aggressive, others are excessively timid. Muzzles have been provided which fit over the heads of aggressive animals and cover their mouths. This may not be a good solution in view of the fact that a muzzle may serve to aggravate the animal. In the light of this, there is a need for alternative solutions for calming excessively aggressive or timid pets.

U.S. Pat. No. 5,874,459 discloses that anandamide may act as a ligand which interacts with cannabinoid receptors in the central nervous system and gut (CB1 receptors) and/or immune cells and tissues such as spleen, thymus and lymphocytes (CB2 receptors). Furthermore, this document indicates that interactions between anandamide and these two types of cannabinoid receptors have been shown to induce physiological effects. It is described that non-arachidonoyl NAEs and NAAs have been shown to inhibit anandamide inactivating enzyme. This inhibition has the net effect of potentiating the effect of anandamide.

It has been suggested that a family of NAEs and NAAs as well as sn-1 and sn-2 monoarachidonyl glycerides are agonists of anandamide receptors (here anandamide receptor refers to a receptor that anandamide might bind to, including CB1, CB2, non-CB receptors) and elicit responses analogous to that elicited by anandamide. The chemical structures of NAEs and NAAs are based on fatty acids and depending on the specific fatty acids esterified they have been shown to have different activities. For example, whereas anandamide interacts with both the CB1 receptor of the central nervous system and the CB2 receptor of the immune system, palmitolyethanolamide may interact with the CB2 receptor but not the CB1 receptor and has an anti-inflammatory effect but no known neural effect.

Nature, vol 396, page 636, (1998) discloses the results of an analysis wherein NAEs and 2 arachidonylglycerol (2-AG) were identified from foods including human, bovine and goat milk and cocoa at various stages of processing. The document suggests that anandamide (300 mgkg body weight$^{-1}$) and 2-arachidonoyl glycerol (400 mgkg body weight$^{-1}$) have bioactivity when taken orally in mice, however the compounds were active only at very high concentrations relative to the concentrations normally present in foods and the results obtained show that the amounts of anandamide, 2-AG and oleamide in foods, including milk and cocoa, are several orders of magnitude below those required if administered by mouth, to reach the blood and cause observable "central effects". However, the document indicates that pure doses of anandamide, 2-AG and oleamide have calming effects and effects on the immune system when injected into animals. Calming effects are characterised by lessened activity, decreased nociception and greater propensity for sleep.

U.S. Pat. No. 5,689,55 discloses that synthetically produced polyunsaturated fatty acid amides and their derivatives are able to mimic the effect of naturally occurring anandamides in the brain and bind to the canabinoid receptor. The compounds described exhibit physiological activity and are reported as being useful active ingredients in pharmaceutical compositions for treatment of inflammation, migraines, spasticity, glaucoma and multiple sclerosis.

Remarkably it has now been found that a composition for oral administration may be provided which includes a precursor that is metabolised endogenously to form a compound having anandamide activity. It is particularly surprising that a dietary precursor is selectively taken up by the CNS and selectively incorporated into the NAE pool to serve as a CB receptor-binding ligand. In addition, it is remarkable that a dietary precursor induces only a small change in the phospholipid acyl composition but induces a large change in the NAE composition.

The invention addresses the problems set out above.

SUMMARY OF THE INVENTION

The present invention provides improved nutritional and therapeutic compositions.

Accordingly, in a first aspect the invention provides a nutritional or therapeutic composition for oral administration which comprises a naturally occurring precursor that is metabolised to a compound having anandamide activity for use as a medicament or nutritive product.

In a second aspect the invention provides a method of production of a nutritional or therapeutic composition for oral administration which comprises the steps of identifying, purifying or synthesising a naturally occurring precursor that is metabolised to a compound having anandamide activity.

In a third aspect the invention provides use of a precursor which is metabolised to a compound having anandamide activity in the manufacture of a nutritional or therapeutic composition for the treatment or prevention of an anandamide-mediated ailment selected from the group which comprises hypertension, glaucoma, insomnia, pain, inflammation, migraine headaches, loss of appetite, nausea, cramps, diarrhea, gut upsets, intestinal motility disturbances, asthma, nervousness, aggressive behaviour, excessive timidity, inability to sleep, catalepsy, low mood, depression, spasms, poor motor control, tics, excessive stress, spasticity, multiple sclerosis and vocalization, poor language acquisition, skin inflammation and excess nociception.

Vocalization is taken to mean disturbances in vocalization and vocalization related to bonding behaviour, for example between an infant and mother. Such vocalizations are important in animal husbandry and in successful nurturing of the offspring by the mother in household pets. Further, such behaviours as chronic sustained crying in human infants may be treatable by oral administration of an embodiment of a composition according to the invention.

Oral administration of an embodiment of a composition according to the invention may also be used to treat or prevent inflammation in superficial mammal tissues (e.g., skin) by modulating levels of compounds with anandamide-like activity in these tissues.

In a forth aspect the invention provides a method of treatment of an anandamide-mediated ailment selected from the group which comprises hypertension, glaucoma, insomnia, pain, inflammation, migraine headaches, loss of appetite, nausea, cramps, diarrhea, gut upsets, intestinal motility disturbances, asthma, nervousness, aggressive behaviour, excessive timidity, inability to sleep, catalepsy, low mood, depression, spasms, poor motor control, tics, excessive stress, spasticity, multiple sclerosis and vocalization, poor language acquisition, skin inflammation and excess nociception which comprises administering an effective amount of an embodiment of the composition according to the invention.

Preferably the precursor that is metabolised to a compound having anandamide activity comprises a long chain polyunsaturated fatty acid (LCPUFA) or derivative thereof. More preferably it comprises a compound of the general formula X:

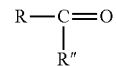

wherein R is the alkenyl moiety of a LCPUFA of total chain length 16-28 carbon atoms with 2-6 double bonds, with the first double bond at the c-1, c-3 c6, c7, c9 c12 position, counting from the non carboxyl (methyl) part of the molecule; and where R" is selected from —H, lower alkyl, —OH, NH$_3$, and NHCH$_2$CH$_2$OH, or an acid addition salt or complex thereof.

More preferably the precursor comprises a plurality of the formula X. Preferably 1-3 X molecules are esterified to a glycerol backbone, in the following stereochemical configurations: sn-1,2,3; sn-1,2; sn-1,3; sn-2,3; sn-1; sn-2; sn-3.

In an alternative embodiment the LCPUFA is a polyunsaturated fatty acid of 16-28 carbon atoms with 2-6 double bonds, having methylated-, branched-, cyclic-, conjugated-, non-methylene interrupted-, epoxy-, furanoid-, hydroxyl-, allylic-, trans-, and seleno-moieties.

More preferably the fatty acid is selected from the group which comprises arachidonate (20:4n-6 AA), linoleate (18:3n-6), gamma linolenate (18:3n-6), dihomogamma-linolenate (20:3n-6 DGLA), adrenic acid (22:4n-6), linolenate (18:3n-3), stearidonic (18:4n-3), eicosatetraenoic (20:4n-3), eicosapentaenoate (20:5n-3), docosahexaenoate (22:6n-3DHA), docosapentaenoate (22:5n-3 or 22:5n-6), tetracosapentaenoate (24:5n-3 or 24:5n-6), tetracosahexaenoate (24:6n-3) or the Mead acid (20:3n-9).

Preferably, an embodiment of a composition according to the invention includes an inhibitor of anandamide inactivating enzyme (also known as amidase). Preferably the inhibitor is selected from the group which comprises oleate and oleamide, palmitate, palmitoylethanolamide, linoleylethanolamide, 2 palmitoylglycerol, 2-linoleylglycerol.

Preferably an embodiment of a composition according to the invention comprises a mixture of a saturated molecule in combination with an unsaturated precursor that is metabolised to a compound having anandamide activity. Preferably, the saturated molecule is palmitate or palmitoylethanolamide. Preferably the unsaturated precursor is arachidonic acid. This provides the advantage that the anandamide activity of the metabolite formed endogenously is potentiated by both inhibiting the breakdown of a metabolite having anandamide-like activity and by the saturated NAE compound binding to the CB2 receptor.

Preferably, an embodiment of a composition according to the invention comprises a mixture of a compound which reacts with a CB receptor in combination with a precursor that is metabolised to a compound having anandamide activity and an inhibitor of the amidase. This provides the advantage of synergy between the active molecules and potentiation of their effect by inhibiting the breakdown of a metabolite having anandamide-like activity.

Preferably, the precursor that is metabolised to a compound having anandamide activity is a free fatty acid, fatty acid ester of an alcohol, or a triacylglycerol. More preferably it is a triacylglycerol having an active fatty acid at the sn-1 and sn-2 position. This provides the advantage that it leads to particularly effective CB receptor agonism. Most preferably, the triacylglycerol comprises both the active precursor compounds (e.g. arachidonate) and the potentiator compounds (e.g. palmitate). This provides the advantage of a particularly effective mixture.

Preferably, an embodiment of a composition according to the invention comprises a structured triacylglycerol prepared by the interesterification of triacylglycerols with active fatty acids so that a bioactive fatty acid is found in the sn-2 position of the triacylglycerol. This provides the advantage of optimising delivery of the active FA to body tissues, particularly the brain.

Preferably an embodiment of a composition according to the invention comprises a physiologically acceptable carrier diluent or adjuvant.

Preferably an embodiment of a composition according to the invention comprises a combination of a naturally occurring precursor that is metabolised to a compound having anandamide activity together with a typical steroidal or non-steroidal anti-inflammatory drug (NSAID). This provides the advantage that synergy occurs since the combination has the ability to diminish inflammation via different pathways.

Preferably, an embodiment of a composition according to the invention comprises a precursor of a CB1 receptor agonist (e.g. anandamide) in combination with a precursor of a CB2 receptor agonist (e.g. palmitoylethanolamide). This provides the advantage that the anti-pain effect of the metabolites is about 100 times stronger than the effect provided by the metabolites of either precursor individually.

Additional features and advantages of the present invention will be described in and apparent from the detailed description of the presently preferred embodiments and the figures.

DETAILED DESCRIPTION OF THE INVENTION

Figure 1:
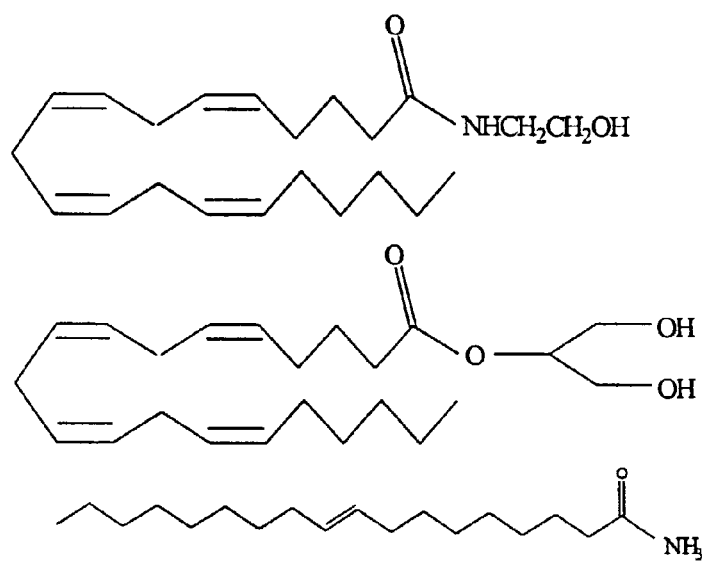
FIG. 1 shows the chemical structure of N-arachidonoyl ethanolamine (anandamide), 2-AG, and oleamide.
Figure 2:
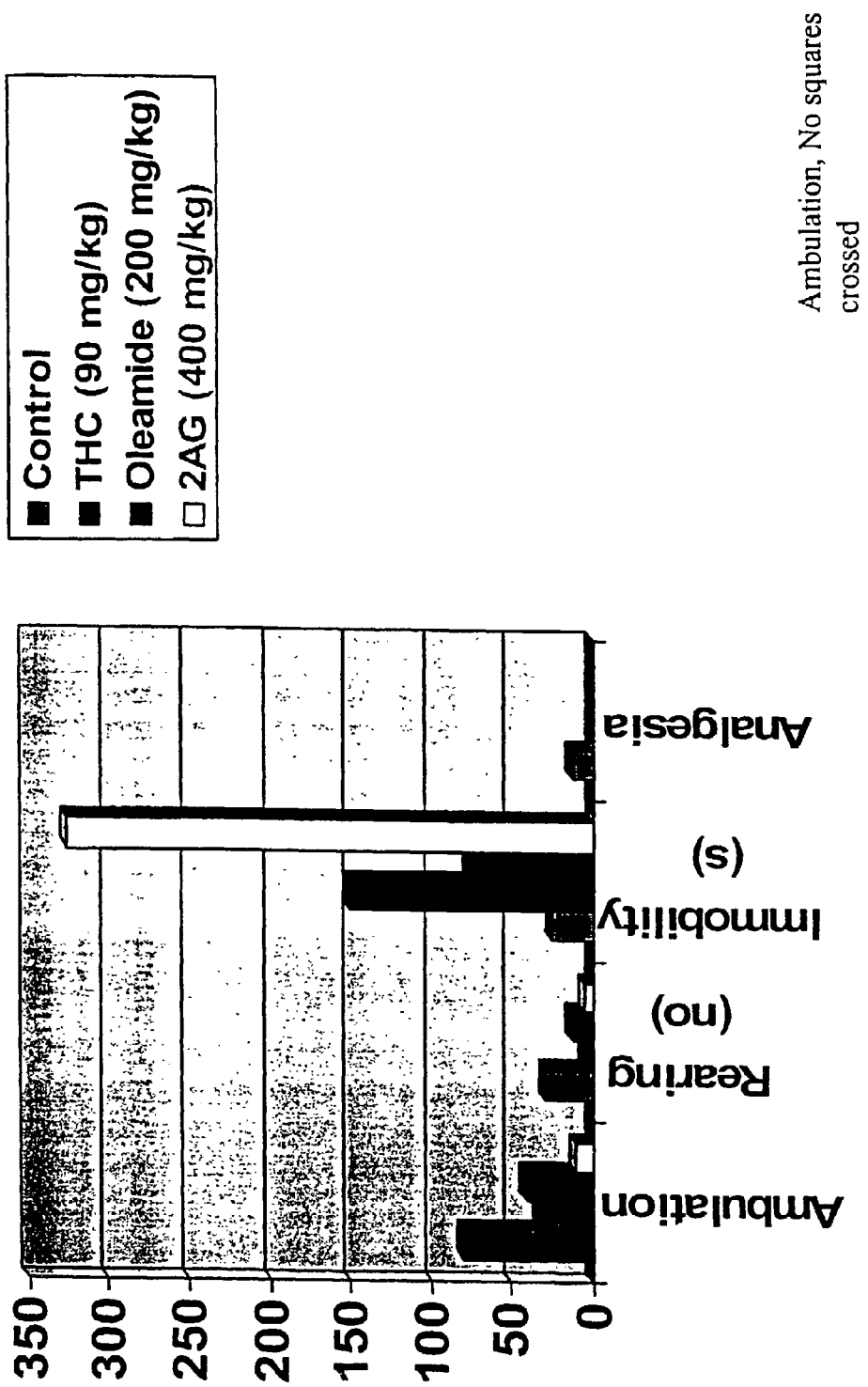
FIG. 2 shows the effects of oral cannabimimetic lipids on ambulation, rearing, immobility and analgesia.
Figure 3:
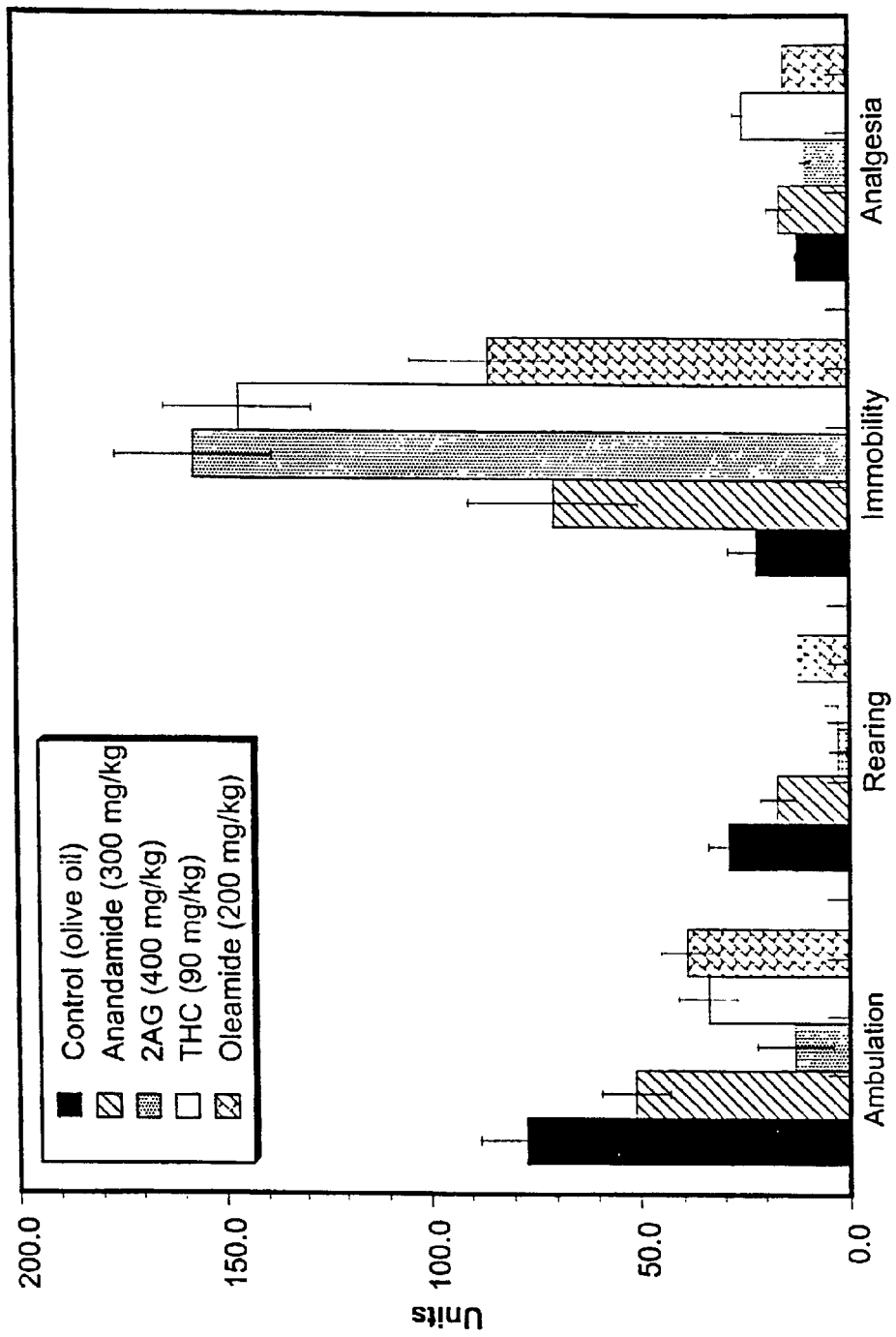
FIG. 3 shows the effects of oral administration of olive oil, anandamide, 2-AG, THC and oleamide on ambulation, rearing, immobility and analgesia. Ambulation, rearing, and immobility parameters were statistically, significantly different between the treatment groups and the control group, $p<0.01$-$0.05$, ANOVA, Newman-Keuls; Only THC statistically, significantly increased analgesia.
Figure 4:
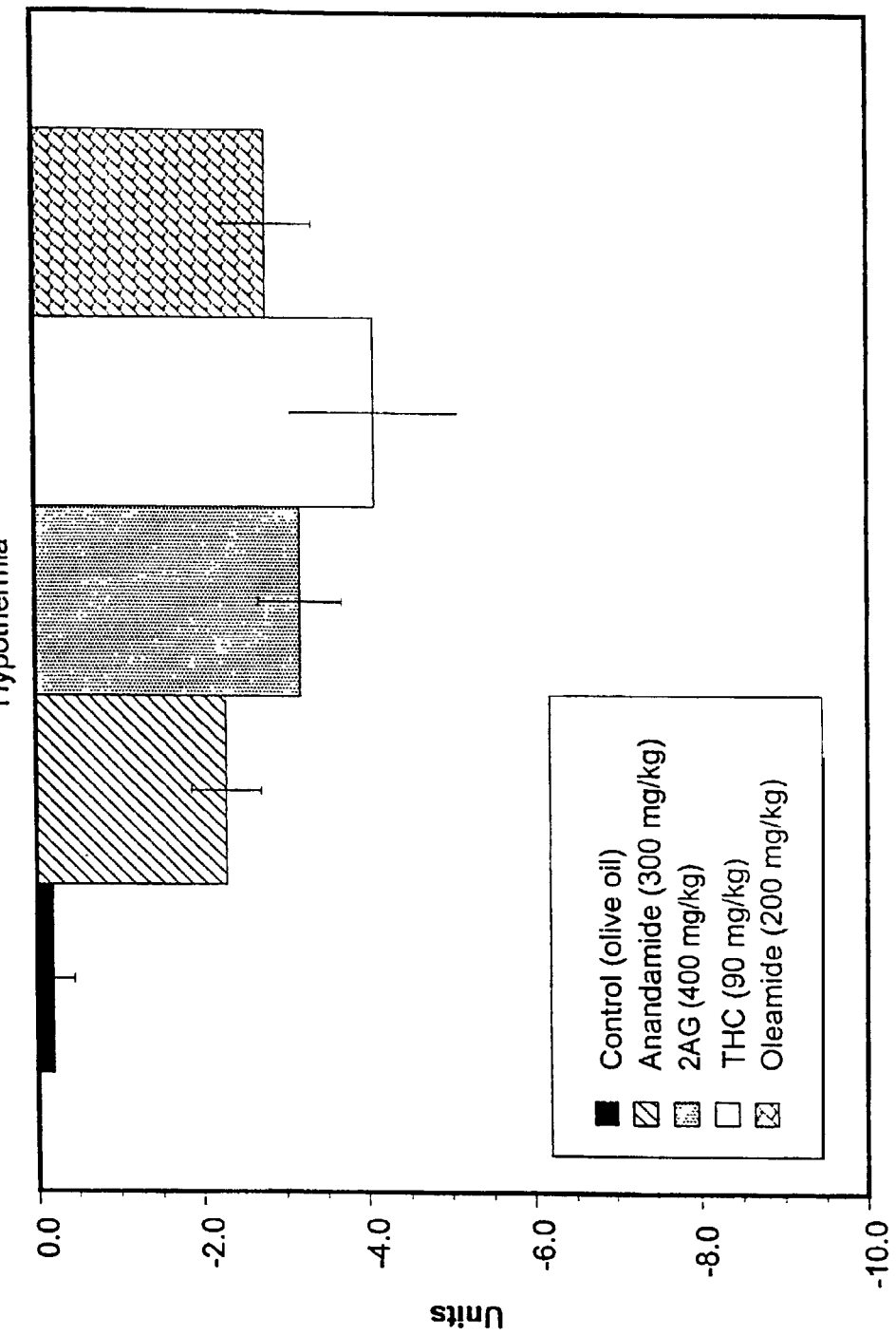
FIG. 4 shows the effect of olive oil, anandamide, 2-AG, THC and oleamide on body temperature. All groups were statistically, significantly different from the control group, $p<0.01$-$0.05$, ANOVA, Newman-Keuls.
Figure 5:
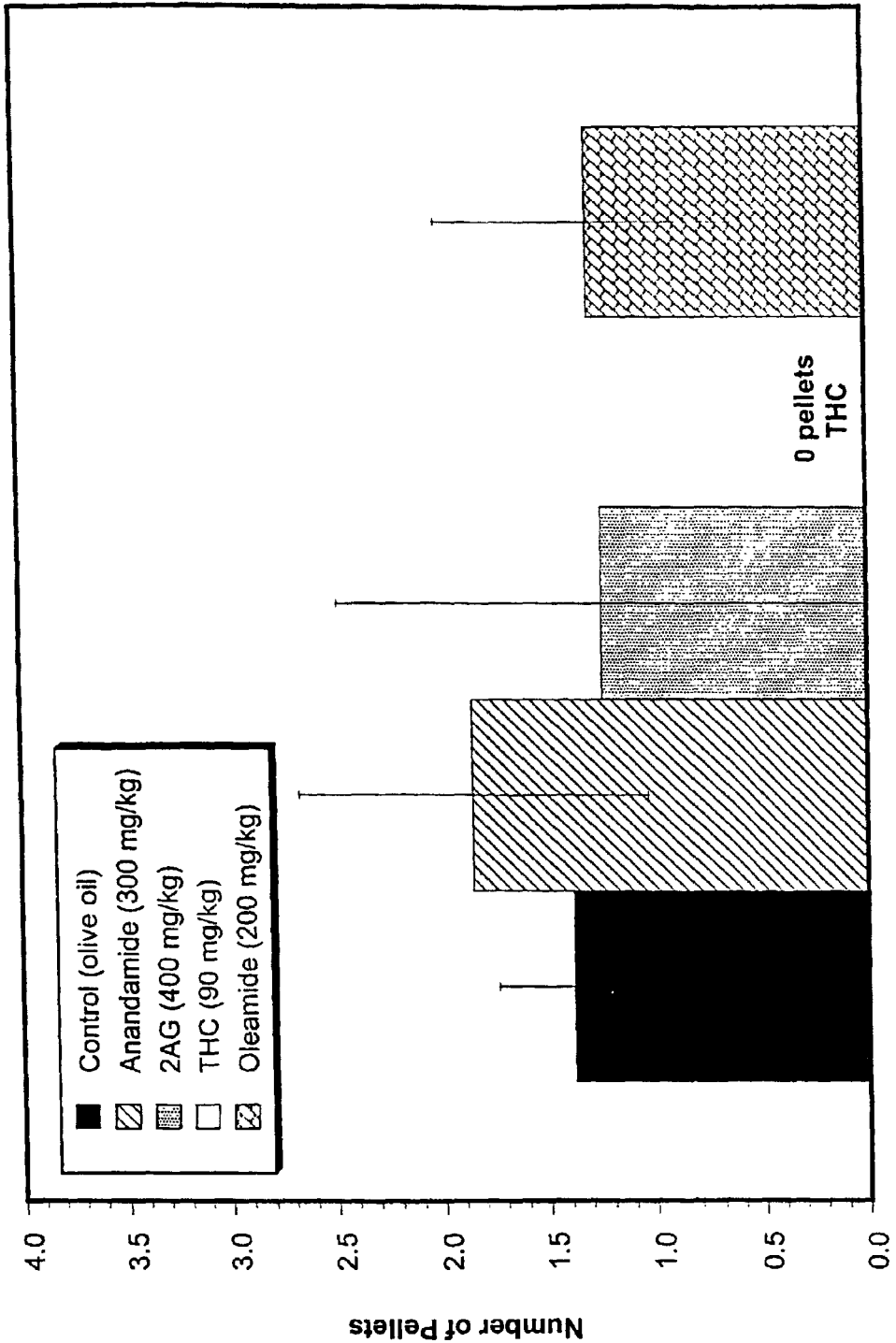
FIG. 5 shows the effect of olive oil, anandamide, 2-AG, THC and oleamide on fecal output. Only the THC group was statistically, significantly different from the control.
Figure 6:
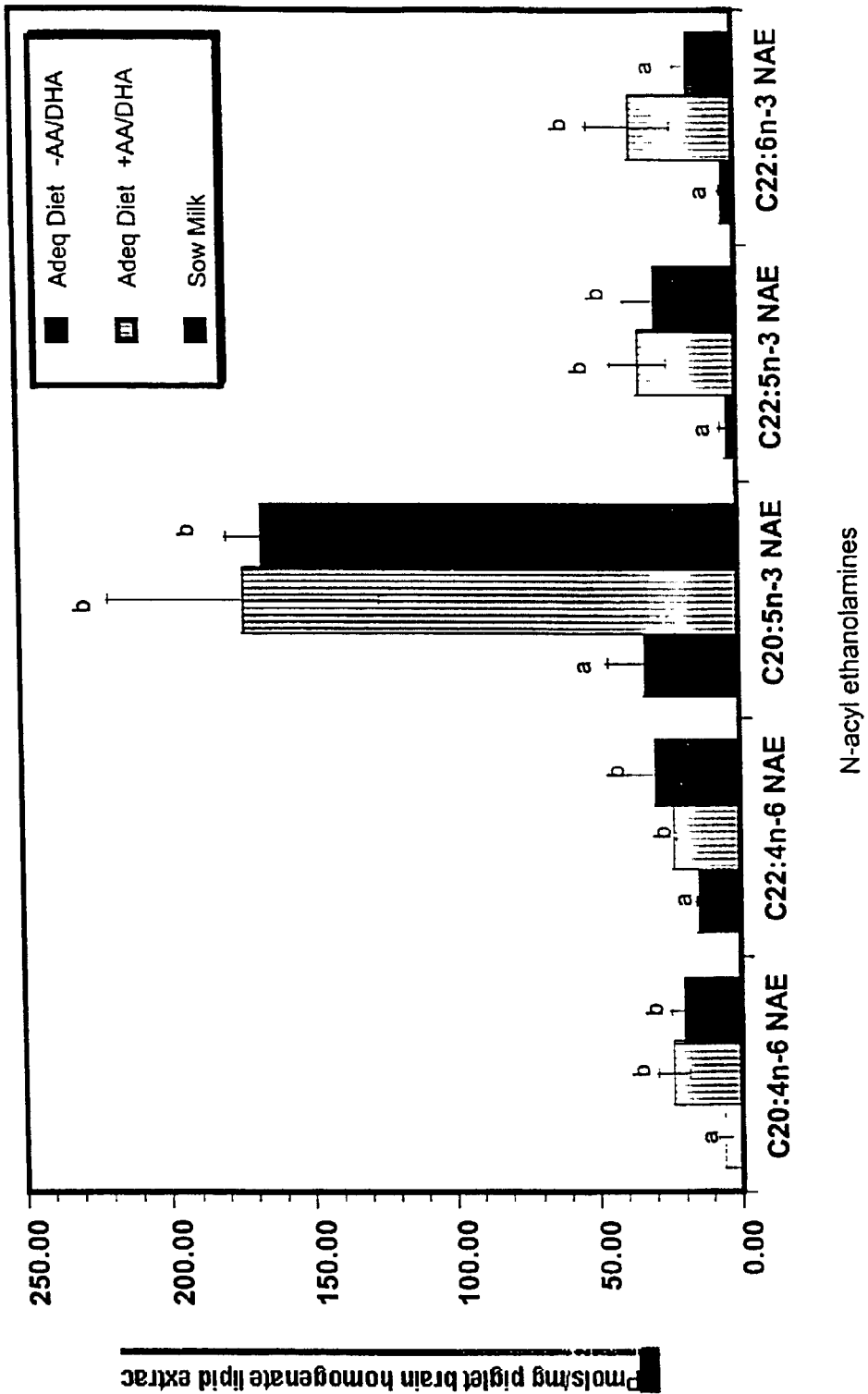
FIG. 6 shows the changes in piglet brain N-acylethanolamines following dietary fatty acid modification with a scale of 0 to 250 on the axis labelled pmols/mg piglet brain lipid extract. Bars within a group of three not denoted with a letter in common are statistically significant from one another ($p<0.01$-$0.05$, ANOVA, Newman-Keuls). Adeq, adequate.
Figure 7:
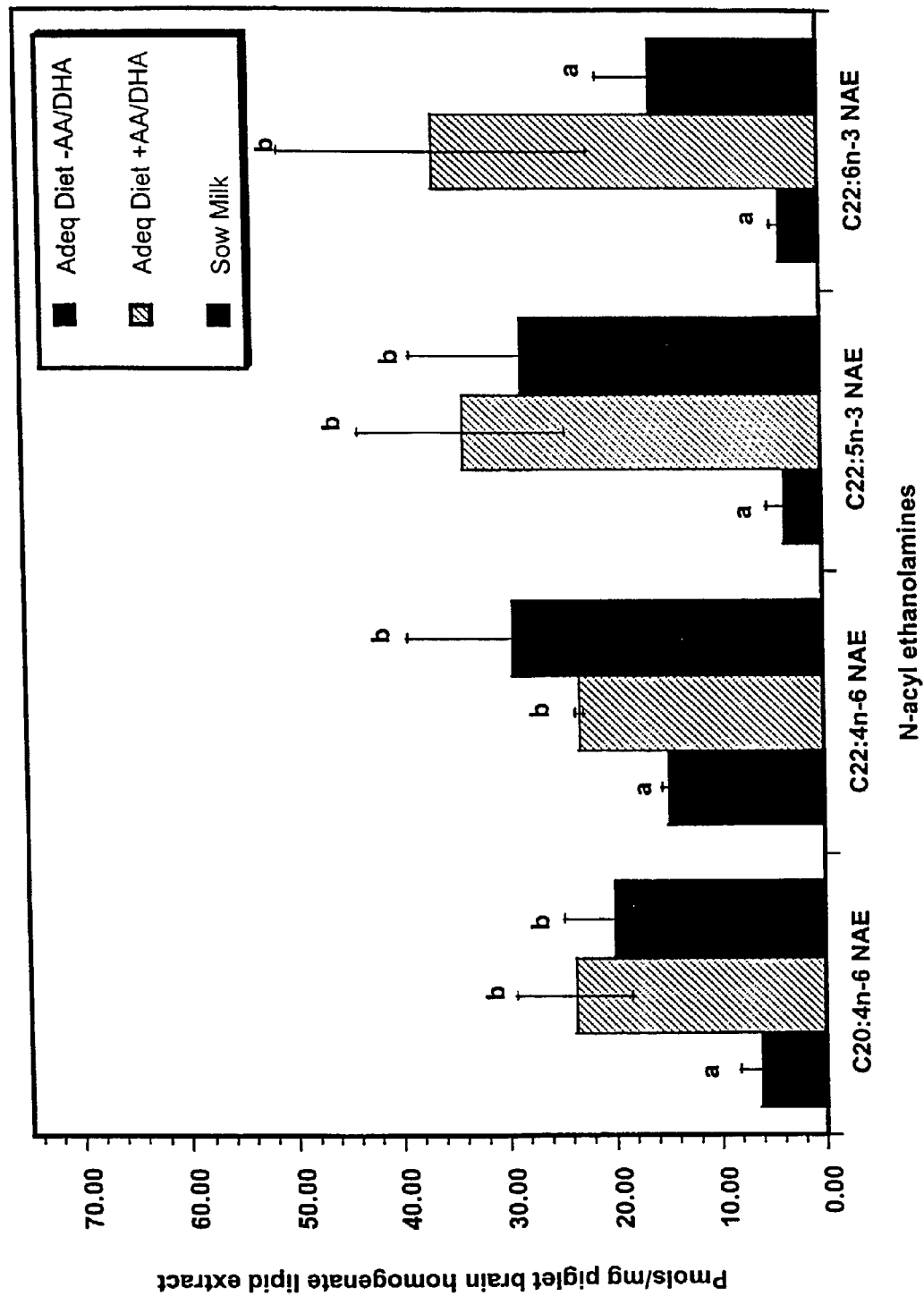
FIG. 7 shows the changes in piglet brain N-acylethanolamines following dietary fatty acid modification with a scale of 0 to 70 on the axis labelled pmols/mg piglet brain lipid extract. Bars within a group of three not denoted with a letter in common are statistically significant from one another ($p<0.01$-$0.05$, ANOVA, Newman-Keuls). Adeq, adequate.

The present invention provides improved nutritional compositions. These compositions provide therapeutic benefits. The compositions include a naturally occurring precursor that is metabolized to a compound having anandamide activity.

By way of example and not limitation, examples of the present invention will now be set forth.

Piglets were fed using two different kinds of adapted infant formulations supplemented with low levels of arachidonate and docosahexaenoate (approximately the same levels as found in human breast milk) and obtained from different sources (see Table 1). The levels of NAE, MAG (monoacylglycerol) and primary amides were evaluated in their brains.

In this study piglets were fed from birth to 18 days with diets comprising embodiments of a composition according to the invention with or without 0.5% 20:4n-6 from single cell oils and 0.4% 22:6n-3 in formula, with either low (deficient) 18:2n-6(1.6%) and 18:3n-3(0.1%), or with adequate 18:2(n-6)(15.6%) and 18:3n-3(1.5%).

The diet compositions are shown in table 1.

TABLE 1

| | Formulas varied in n-3 and n-6 fatty acid content | | | | | | |
|---|---|---|---|---|---|---|---|
| | 18:2n-6-18:3n-3 deficient | | | 18:2n-6-18:3n-3 adequate | | | |
| Fatty Acid | No LCP | Egg + fish Oil | Single cell oil | No LCP | Egg + fish oil | single cell oil | Sow milk |
| | g/100g fatty acids | | | | | | |
| 8:0 | 8.0 | 7.0 | 7.4 | 17.2 | 15.5 | 14.9 | |
| 10:0 | 6.7 | 5.9 | 6.5 | 13.5 | 12.6 | 13.0 | |
| 12:0 | 44.2 | 39.7 | 42.9 | 1.0 | 0.3 | 0.3 | 0.1 |
| 14:0 | 17.1 | 15.6 | 16.8 | 0.8 | 0.6 | 0.6 | 2.4 |
| 16:0 | 9.5 | 10.5 | 9.5 | 11.3 | 12.1 | 10.9 | 28.1 |
| 18:0 | 3.4 | 4.0 | 3.5 | 3.2 | 3.5 | 3.3 | 5.6 |
| 16:1 | 0.1 | 0.34 | 0.1 | 0.1 | 0.3 | 0.2 | 4.7 |
| 18:1 | 8.1 | 10.4 | 9.3 | 33.3 | 33.4 | 35.1 | 32.6 |
| 18:2n-6 | 1.6 | 3.8 | 1.9 | 15.6 | 16.0 | 16.4 | 20.4 |

TABLE 1-continued

Formulas varied in n-3 and n-6 fatty acid content

| | 18:2n-6-18:3n-3 deficient | | | 18:2n-6-18:3n-3 adequate | | | |
|---|---|---|---|---|---|---|---|
| Fatty Acid | No LCP | Egg + fish Oil | Single cell oil | No LCP | Egg + fish oil | single cell oil | Sow milk |
| 18:3n-6 | — | 0.6 | 0.1 | — | 0.4 | 0.1 | 0.2 |
| 20:2n-6 | — | — | — | — | — | — | 0.4 |
| 20:3n-6 | — | — | — | — | — | — | 0.2 |
| 20:4n-6 | — | 0.1 | 0.4 | — | 0.1 | 0.4 | 0.7 |
| 22:4n-6 | — | — | — | — | — | — | 0.1 |
| 18:3n-3 | 0.1 | 0.5 | 0.1 | 1.5 | 1.8 | 1.6 | 2.3 |
| 20:5n-3 | — | 0.1 | — | — | 0.1 | — | 0.1 |
| 22:5n-3 | — | — | — | — | — | — | 0.6 |
| 22:6n-3 | — | 0.3 | 0.3 | — | 0.3 | 0.3 | 0.1 |

Changes in individual brain phospholipid classes that occurred after feeding were analysed.

The results showed that the addition of 20:4n-6 and 22:6n-3 to diets containing adequate levels of essential fatty acids (18:2n-6 and 18:3n-3) lead to an increase in 22:6n-3 in phosphatidyl choline; a decrease in 22:5n-6 in phosphatidyl ethanolamine; and no change in arachidonate (20:4n-6) in any of the phospholipid classes.

Thus, the small, unsubstantial increase seen in 22:6n-3 in phosphatidyl choline is consistent with the fact that the relevant diet had added 22:6n-3; however the lack of significant increase in arachidonate in any of the phospholipid classes examined indicates that added arachidonate is not incorporated into these phospholipid classes, but rather is metabolised or inadequately transported to the brain.

The primary amides, oleamide and arachidonamide, and 18:3 NAE were not detected and are omitted from table 2, which shows the changes in levels of MAG and NAE expressed as pmols/mg lipid that occurred following feeding of the diets.

TABLE 2

Monacyl glycerols (MAG)

| Group | C20:4n-6 | C22:4n-6 | C22:6n-3 |
|---|---|---|---|
| Adequate | 66.0 | 3.53 | 3.87 |
| adequate + SCO | 44.4 | 6.23 | 5.93 |
| Sow fed | 44.1 | 6.13 | 6.67 |

TABLE 3

N-acyl-ethanolamines (NAE)

| Group | C16:0 | C18:0 | C18:1n-9 | C18:2n-6 |
|---|---|---|---|---|
| Adequate | 114.87 | 27.90 | 27.00 | 8.57 |
| adequate + SCO | 149.93 | 63.87 | 15.97 | 2.90 |
| Sow fed | 95.07 | 3.13 | 1.40 | 9.80 |

TABLE 4

N-acyl-ethanolamines (NAE)

| Group | C20:4n-6 | C20:5n-3 | C22:4n-6 | C22:5n-3 | C22:6n-3 |
|---|---|---|---|---|---|
| Adequate | 6.10 | 32.87 | 14.80 | 3.63 | 3.80 |
| adequate + SCO | 23.77 | 172.37 | 23.07 | 33.67 | 36.10 |
| Sow fed | 19.97 | 165.63 | 29.30 | 28.00 | 15.77 |

MAG levels were not statistically significant for 20:4n-6 MAG, 22:4n-6 MAG and 22:6n-3 MAG in animals fed essential fatty acid sufficient diets (sn-1 and 2 isomers combined). This is an important finding because specific MAGs, such as 2-AG are known to bind to CB receptors and have bioactivity.

In animals fed the 18:2n-6/18:3n-3 sufficient diets, supplementation with AA and DHA led to increases in 20:4n-6 NAE and 22:4n-6 NAE (22:4n-6 is the 2-carbon elongation product of AA), 22:6n-3 NAE, 20:5n-3 NAE and 22:5n-3 NAE (the latter two are retroconversion products of 22:6n-3). The levels of these NAE products were similar to that found in sow milk fed piglets. Thus, it is a remarkable feature of the invention that when sufficient essential fatty acids are provided in the diet, the supplementation of AA and DHA to levels found in breast milk, has the effect of increasing corresponding NAE products to levels found in sow milk.

The results obtained indicate that supplementation with AA and DHA to formulae having sufficient essential fatty acid had minimal effects on brain phospholipid acyl moieties. However, in striking contrast, the same level of supplementation led to a 4-fold increase in the level of 20:4n-3 NAE present, a 5.2 fold increase in 20:5n-3 NAE, and a 9.5 fold increase in 22:5n-3 and 22:6n-3 NAE.

In order to show the biological activity of the composition of the present invention on animal's behaviour the effect of dietary poly-unsaturated fatty acids with and without a CB-1 receptor antagonist on anxiolytic-like responses in mice were tested. To this end, the ELEVATED PLUS MAZE TEST was applied (adapted after Handley and Mithani (Naunyn. Schmied. Arch. Pharmacol. 327: 1-5, 1984).

For the experiments male Rj:NMRI mice, obtained from Elevage Janvier, Le Genest-Saint-Isle France and weighing 10-11 g at delivery and 33-51 grams on day 42 were used. The mice were housed 10 per cage in wire cages with bedding and normal light cycle. They received ad libitum quantities of bottled distilled water and purified powdered diets (7.5 g/mouse) in ceramic cups (10/group) for 42 days. The Food was maintained at −80° C. in daily aliquots under nitrogen, thawed each afternoon before administration to mice. Uneaten food was discarded daily.

The principle of the test resides in that anxiolytic agents increase the number of entries into the open and often the closed arms of the elevated Consequently, mice should want to move and explore the spaces of the open and closed arms rather than staying still in the middle).

Mice were given the following agents intraperitoneally 60 minutes before the Plus Maze test:

Tween 80 as placebo;

the anxiolytic agent Clobazam at a non-sedative dose for test validation; or validated amounts of AM251 (Tocris Cookson LTD., UK), a CB-1 receptor antagonist, to inhibit binding of endogenous NAEs to the CB-1 receptor.

All diets contained 90% fat-free AIN93G rodent diet in powder form (Lot 9350-5, Dyets, Inc., Bethlehem, Pa.), 0.4% milk fat, 1.2% palm olein, 1.9% Trisun sunflower oil, 1.5% soybean oil and 2.1-5.1% medium chain triacylglycerol oil. Parts of the medium chain triacylglycerol oil were replaced with 1.1% algal oil (providing 0.5 dietary wt.-% arachidonic acid) in diet D, 1.9% fish oil (providing 0.5 dietary wt.-% docosahexaenoic acid) in diet E, and with 1.1% algal oil and 1.9% fish oil in diets F and G. Dietary groups are summarized in the table below:

| Diet Code | Diet Description | Agent given before Plus Maze Test |
|---|---|---|
| A | Control Diet | Tween 80, 1% distilled water solution |
| B | Control Diet | Clobazam, 32 mg/kg body weight |
| C | Control Diet | AM 251, 64 mg/kg body weight |
| D | Diet AA | Tween 80, 1% distilled water solution |
| E | Diet DHA | Tween 80, 1% distilled water solution |
| F | Diet AA + DHA | Tween 80, 1% distilled water solution |
| G | Diet AA + DHA | AM 251, 64 mg/kg body weight |

Abbreviations: AA, Arachidonic Acid; DHA, Docosahexaenoic Acid

The body weight, weight gain and the food intake of the mice was monitored throughout the experiment. These parameters were not significantly affected by ingestion of the various diets using classical one way analysis of variance (ANOVA). This indicates that differences in the behavioral tests as found can only be attributed to the components in the diet that were varied, namely dietary polyunsaturated fatty acids. To assess changes in the Plus Maze test, generalized Linear Models (GLM) and the Poisson family were used because the obtained response data are non-normally distributed counts.

Number of Entries in the Closed Arms

A vs. B: Average entries were 3.6 and 6.3, respectively, and the difference is at the limit of statistical significance (p-value=0.053). This result establishes that the anxiolytic agent Clobazam, under the present conditions, can increase closed arm entries.

| | |
|---|---|
| A vs. C | There was no significant difference (p-value = 0.19). |
| A, D, E and F | overall, the p-value is 0.06. The fitted average entries are respectively 3.6, 6.4, 6.0 and 6.8. In group D, there is one mouse with 16 entries, which is unusally high. Omitting this mouse, the p-value becomes significant (0.02) and the prediction for group |
| D | decreases to 5.3. This result establishes that the combination of dietary AA and DHA may induce anxiolytic (Clobazam-like) effects. |
| F vs. G | Average entries are respectively 6.8 and 4.6, and the difference is at the limit of statistical significance (p-value = 0.11). This result indicates that the anxiolytic effects of the combination of dietary AA and DHA may be transduced via CB-1 receptor binding, i.e., via binding of PUFA-derived NAEs. |
| C vs. G | Average entries are respectively 2.3 and 4.6, and the difference is close to statistical significance (p-value = 0.08). This result indicates that CB-1 receptors are not the only receptors that mediate responses in the PLUS MAZE TEST, i.e., non-CB-1 receptors may partially mediate the actions of dietary PUFA and (PUFA-derived) NAEs. Additionally, the drug AM251 may not fully antagonize CB-1 receptor binding. |

In summary, the results from the number of entries into the closed arms in the ELEVATED PLUS MAZE TEST show that dietary AA and DHA and the combination of the two, have anxiolytic-like effects that seem to be mediated via their conversion to NAEs, and these NAEs in turn bind to CB-1 receptors located in brain regions known to induce behavioral responses in the PLUS MAZE TEST, such as the hippocampus.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

The invention claimed is:

1. An orally administrable composition comprising a steroidal or non-steroidal anti-inflammatory drug ("NSAID"), and a structured triacylglycerol comprising: a naturally occurring precursor portion at the sn-2 position of the structured triacylglycerol, wherein the naturally occurring precursor portion is metabolised to a compound having anandamide activity for use as a medicament, and an inhibitor of an anandamide inactivating enzyme (amidase) in at least one position selected from the group consisting of the sn-1 position and the and sn-3 position of the structured triacylglycerol, wherein the naturally occurring precursor comprises a fatty acid selected from the group consisting of arachidonate (20:4n-6 AA) and docosahexaenoate (22:6n-3DHA), and wherein the inhibitor comprises palmitoylethanolamide.

2. A composition according to claim 1 wherein the structured triacylglycerol further comprises a naturally occurring precursor portion at the sn-1 or sn-3 position.

3. A composition according to claim 1 wherein the structured triacylglycerol comprises a naturally occurring precursor at the sn-1 and sn-2 positions, or at the sn-2 and sn-3 positions.

4. A composition according to claim 1 wherein the precursor comprises the acyl portion of arachidonate (20:4n-6 AA).

5. A composition according to claim 1 wherein the structured triacylglycerol comprises palmitoylethanolamide at the sn-3 position and arachidonate at the sn-1 and sn-2 positions.

6. A composition according to claim 1 which comprises a physiologically acceptable carrier, diluent or adjuvant.

7. A method for producing a nutritional or therapeutic composition for oral administration comprising the steps of obtaining a therapeutically effective amount of a naturally occurring precursor that is metabolised to a compound having anandamide activity, obtaining a steroidal or non-steroidal anti-inflammatory drug (NSAID), obtaining an inhibitor of an anandamide inactivating enzyme (amidase), and preparing a composition including the steroidal or non-steroidal anti-inflammatory drug (NSAID), and a structured triacylglycerol comprising the precursor at the sn-2 position, and the inhibitor in at least one position selected from the group consisting of the sn-1 and the sn-3 position of the structured triacylglycerol,
wherein the precursor comprises a fatty acid selected from the group consisting of arachidonate (20:4n-6 AA) and docosahexaenoate (22:6n-3DHA), and wherein the inhibitor comprises palmitoylethanolamide.

8. A method of manufacturing a composition for the treatment of an anandamide-mediated ailment, the method comprising preparing a composition comprising a steroidal or non-steroidal anti-inflammatory drug (NSAID), and a structured triacylglycerol comprising a naturally occurring precursor at the sn-2 position of the structured triacylglycerol that is metabolised to a compound having anandamide activity for use as a medicament, and an inhibitor of an anandamide inactivating enzyme (amidase) in at least one position selected from the group consisting of the sn-1 and the and sn-3 position of the structured triacylglycerol, wherein the precursor comprises a fatty acid selected from the group consisting of arachidonate (20:4n-6 AA) and docosahexaenoate (22:6n-3DHA), and wherein the inhibitor comprises palmitoylethanolamide.

9. A method of treating an anandamide-mediated ailment, the method comprising administering to a patient having an anandamide-mediated ailment an effective amount of a composition comprising a steroidal or non-steroidal anti-inflammatory drug (NSAID), and a structured triacylglycerol comprising a naturally occurring precursor at the sn-2 position of the structured triacylglycerol that is metabolized to a compound having anandamide activity for use as a medicament, and an inhibitor of an anandamide inactivating enzyme (amidase) in at least one position selected from the group consisting of the sn-1 position and the sn-3 position of the structured triacylglycerol, wherein the precursor comprises a fatty acid selected from the group consisting of arachidonate (20:4n-6 AA) and docosahexaenoate (22:6n-3DHA), and wherein the inhibitor comprises palmitoylethanolamide.

10. A method of claim 7 wherein the method includes the step of purifying the naturally occurring precursor.

11. A method according to claim 9 wherein the structured triacylglycerol comprises a naturally occurring precursor at the sn-1 and sn-2 positions, or at the sn-2 and sn-3 positions.

* * * * *